United States Patent [19]

Das et al.

[11] Patent Number: 4,522,949

[45] Date of Patent: Jun. 11, 1985

[54] 7-OXABICYCLOHEPTANE SUBSTITUTED PROSTAGLANDIN INTERPHENYLENE ANALOGS USEFUL AS CARDIOVASCULAR AGENTS

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 543,681

[22] Filed: Oct. 20, 1983

[51] Int. Cl.³ .................... A61K 31/34; C07D 307/00
[52] U.S. Cl. .................................. 514/469; 549/463
[58] Field of Search ...................... 549/463; 424/285

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/459 |
| 4,228,180 | 10/1980 | Sprague | 424/285 |
| 4,254,044 | 3/1981 | Sprague | 549/463 |
| 4,463,015 | 7/1984 | Haslanger et al. | 549/463 |

FOREIGN PATENT DOCUMENTS 0043292 8/1982 European Pat. Off. .
2039909 8/1980 United Kingdom .

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

7-Oxabicycloheptane substituted interphenylene prostaglandin analogs are provided having the structural formula

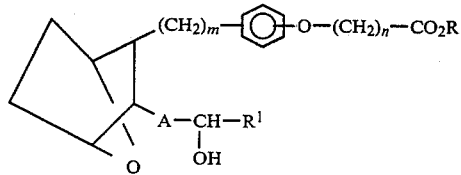

and including all stereoisomers thereof.

The compounds are cardiovascular agents useful, for example, in the treatment of thrombolytic disease.

12 Claims, No Drawings

7-OXABICYCLOHEPTANE SUBSTITUTED PROSTAGLANDIN INTERPHENYLENE ANALOGS USEFUL AS CARDIOVASCULAR AGENTS

DESCRIPTION OF THE INVENTION

The present invention relates to 7-oxabicycloheptane prostaglandin interphenylene analogs which are cardiovascular agents useful, for example, in the treatment of thrombolytic disease. These compounds have the structural formula

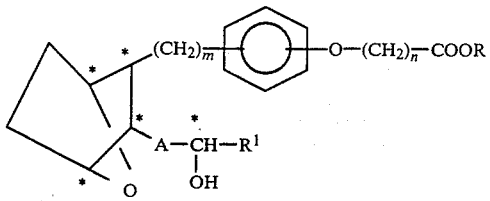

and including all stereoisomers thereof, wherein A is —CH=CH— or $(CH_2)_2$, m is 1 to 4; n is 1 to 8; R is H, lower alkyl or alkali metal; and $R^1$ is lower alkyl, aryl, aralkyl, cycloalkyl or cycloalkylalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 to 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralykyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The terms "$(CH_2)_m$" and "$(CH_2)_n$" includes a straight or branched chain radical having from 1 to 4 carbons in the normal chain in the case of "$(CH_2)_m$" and 1 to 8 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$,

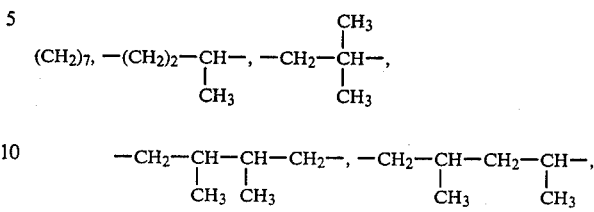

Preferred are those compounds of formula I wherein A is CH=CH, m is 1, R is H, n is 1 or 2, and $R^1$ is lower alkyl, aryl, such as phenyl or aralkyl such as benzyl.

The various compounds of the invention may be prepared as outlined below.

Compounds of formula I wherein m is 1 and A is CH=CH, that is,

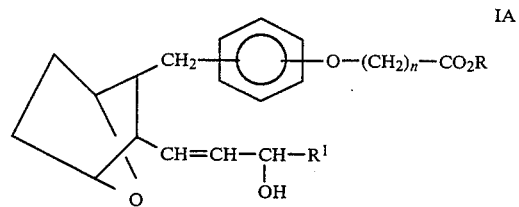

may be prepared according to the following reaction description.

The mesoanhydride

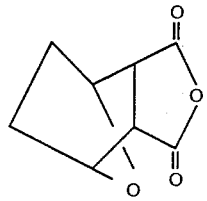

prepared as described in U.S. Pat. Nos. 4,143,054 and 4,220,594, is reduced by reaction with a reducing agent such as lithium aluminum hydride or diisobutylaluminum hydride in the presence of an inert organic solvent such as tetrahydrofuran, toluene or ether, to form the diol B

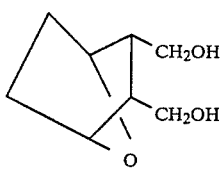

The diol B is then subjected to a chloroformylation reaction by reacting B with phosgene in the presence of an inert organic solvent such as tetrahydrofuran, ether or methylene chloride and an aromatic solvent such as toluene or benzene, to form alcohol C

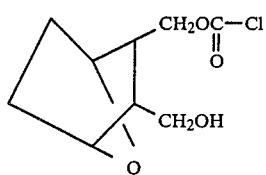

C which is converted to a cyclic-carbonate D by treating alcohol C with pyridine or other organic base, such as triethylamine or diazabicycloundecane in the presence of dichloromethane, ether or chloroform to form D

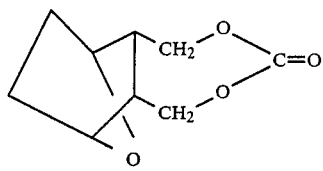

D

The cyclic-carbonate D is then reacted with an alkanol (alkyl-OH) such as isopropanol, ethanol or methanol to form the alcohol II

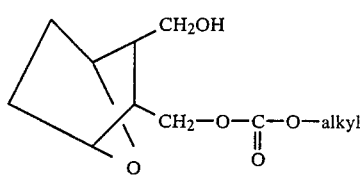

II which is then oxidized by reacting II with pyridinium chlorochromate in the presence of sodium acetate and dichloroemethane to form the alkedyde III

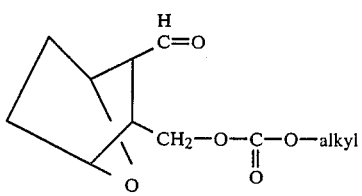

III

Aldehyde III is then subjected to a Grignard reaction by reacting same with magnesium and a halogenated aromatic derivative such as 3-bromophenylmethoxymethyl ether or other compound of the structure

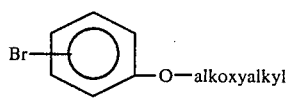

E to form a mixture of alcohol isomers

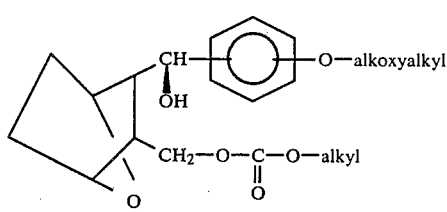

IV

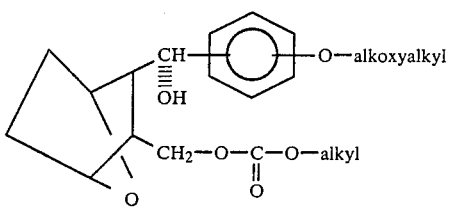

V

The isomers IV and V are separated by conventional means, such as by silica gel column chromatography, and the desired isomer is acylated by reacting same with acetic anhydride in the presence of dimethylaminopyridine and a basic organic solvent such as pyridine to form the acetates VI and VII

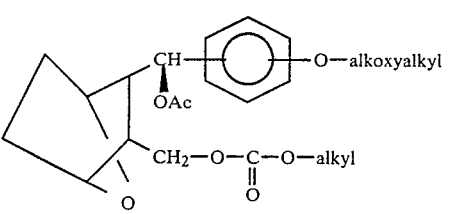

VI

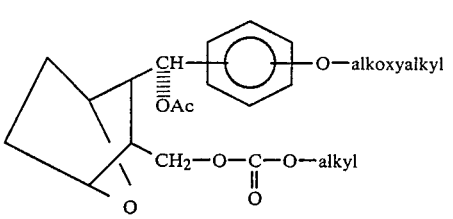

VII which are separated by column chromatography or other conventional means into the separate isomers VI and VII.

The desired isomer is then made to undergo hydrogenolysis by treating VI or VII with palladium on charcoal and hydrogen in acetic acid to form VIII

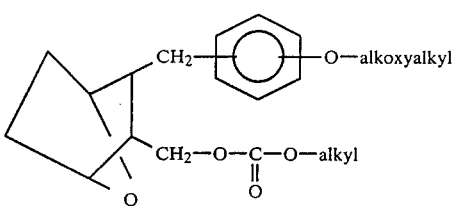

VIII

Compound VIII is then hydrolyzed by treatment with an acid such as HCl in the presence of an inert organic solvent such as tetrahydrofuran to form IX

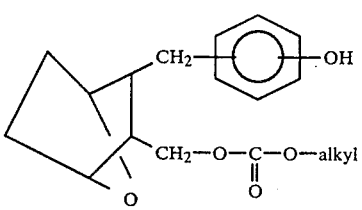

IX which is then subjected to O-alkylation by reaction with a base such as sodium hydride, potassium hydride or potassium carbonate in the presence of a haloalkanoic acid ester

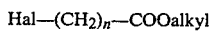
Hal—(CH$_2$)$_n$—COOalkyl and an inert organic solvent such as dimethoxy-ethane to form the ester X

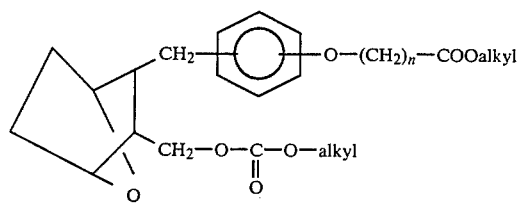

X

The ester X is then hydrolyzed by treatment with a base such as lithium hydroxide, potassium carbonate or sodium hydroxide in the presence of an inert organic solvent such as tetrahydrofuran, methanol or dimethyoxyethane-water to form the acid XI

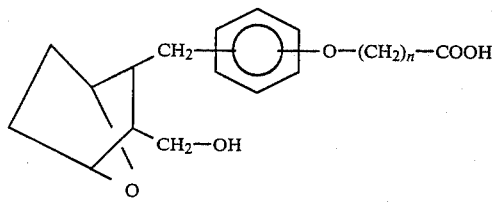

XI

Acid XI is then esterified by treatment with diazomethane or other diazoalkane in the presence of ether as a solvent to form the ester XII

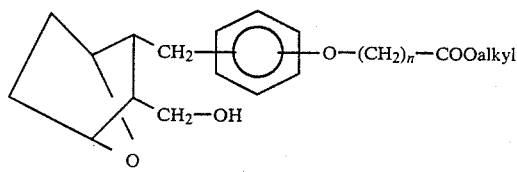

XII

The ester XII is then subjected to a Collins oxidation by reacting XII with chromium trioxide in the presence of a basic solvent such pyridine and dichloromethane to form the aldehyde XIII

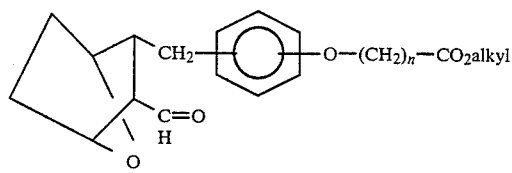

XIII

Thereafter, aldehyde XIII is made to undergo a phosphonate reaction which is carried out by reacting XIII with a phosphonate

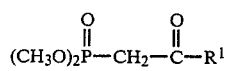
(CH$_3$O)$_2$P(=O)—CH$_2$—C(=O)—R$^1$

F in the presence of a base such as sodium hydride, potassium t-butoxide or potassium hydride to form the ester XIV

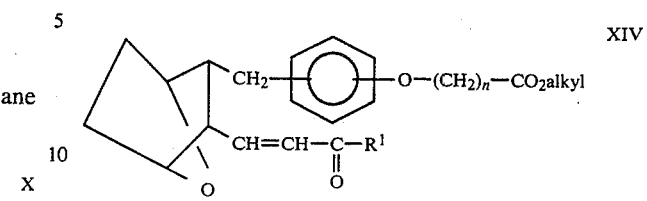

XIV which is then reduced by treating with a reducing agent such as sodium borohydride, sodium cyanoborohydride or other reducing agent, in the presence of cesium chloride and an alkanol such as methanol or ethanol to form the alcohol esters XV and XVI

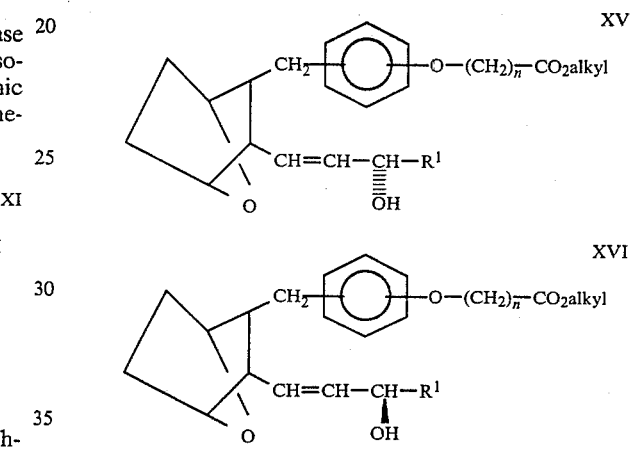

XV

XVI

The above isomers may then be converted to the corresponding acids XVII and XVIII, respectively, by simple hydrolysis by treating with a base such as lithium hydroxide, sodium hydroxide or potassium hydroxide to form the corresponding alkali metal salt and then neutralizing with an acid such as dilute HCl or oxalic acid to form the corresponding acids.

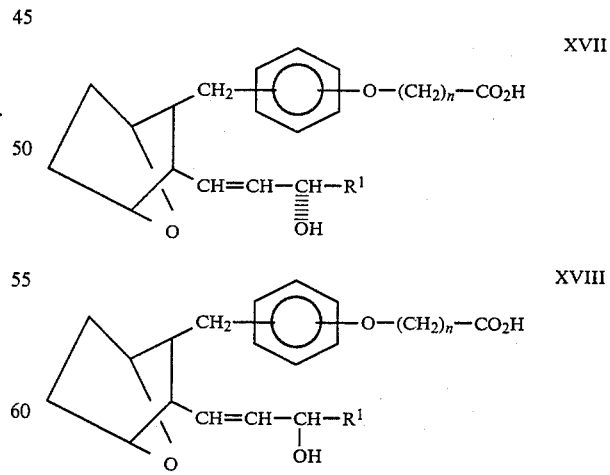

XVII

XVIII

Compounds of formula I wherein m is other than 1, that is, m is 2, 3 or 4, may be prepared by subjecting aldehyde III to a homologation sequence, such as a Wittig reaction with (C$_6$H$_5$)$_3$P=CHOMe followed by hydrolysis (m−1) times. The aldehyde IIIA

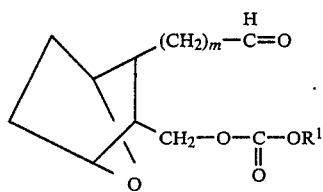

IIIA where m is 2 to 4 is thus carried on to compounds of this invention wherein m is 2 to 4 by subjecting IIIA to a Grignard reaction and so forth as described above with respect to the conversion of aldehyde III to the compounds of the invention.

Compounds of formula I wherein A is —CH$_2$—CH$_2$— may be prepared by reducing ester XIV, with sodium borohydride in a basic solvent like pyridine, triethylamine, collidine or 2,6-dimethyl aniline to form the ester

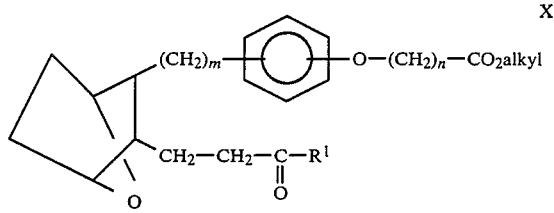

XIX

The ester XIX may then be reduced to the corresponding alcohol

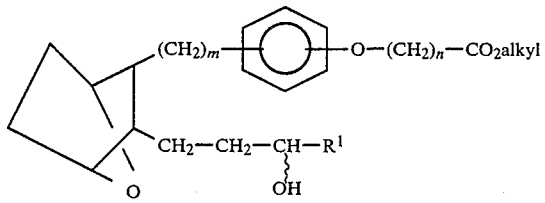

XX as described with respect to compound XV or XVI and then hydrolyzed to the alkali metal salt and ultimately neutralized to the final acid product.

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

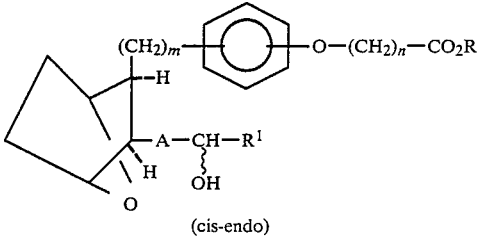

Ia (cis-endo)

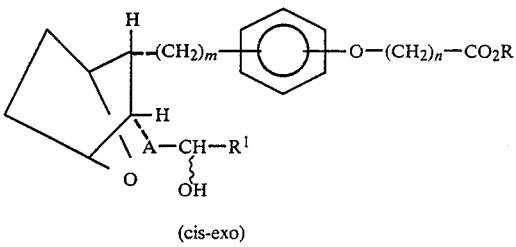

Ib (cis-exo)

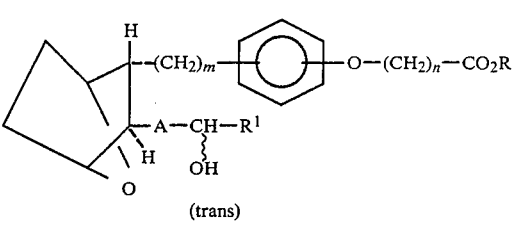

Ic (trans)

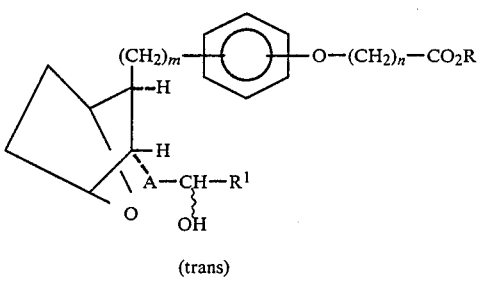

Id (trans)

The wavy ($\}$) line in the above formulae indicates that the hydroxy group in each of the compounds of formulae Ia–Id is either R($\beta$) or S($\alpha$).

The nucleus in each of the compounds of the invention is depicted as

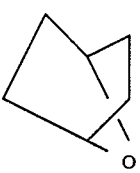

for matter of convenience; it will also be appreciated that the nucleus in the compounds of the invention may be depicted as

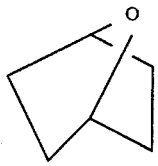

The compounds of this invention are cardiovascular agents useful as platelet aggregation inhibitors, such as archidonic acid-induced platelet aggregation, e.g., for treatment of thrombolytic disease, such as coronary or cerebral thromboses. In addition, the compounds of the invention are useful in inhibiting bronchoconstriction such as associated with asthma. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg. preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptacle vehicle or carrier, excipient, binder, preservative, stabilizer, flavor, etc. as called for by accepted pharmaceutical practice. Also as indicated in the discussion above, certain members additionally serve as intermediates for other members of the group.

The compounds of this invention may also be administered topically to treat peripheral vascular diseases and as such may be formulated as a cream or ointment.

The following Examples represent preferred embodiments of the invention. Unless otherwise indicated, all temperatures are expressed in degrees Centigrade.

EXAMPLE 1

[1α,2β,3β(1E,3R),4β]-[3-[[3-Hydroxy-4,4-dimethyl-1-octenyl)-7-oxabicyclo[2.2.1]hept-2-yl]methyl]phenoxy]acetic acid, methyl ester

A. (1α,2β,3β,4α)-cis-exo-7-oxabicyclo[2.2.1]heptane-2,3-dimethanol

To a suspension of 11.4 g lithium aluminum hydride (300 mmole, 1.6 eq.) in 400 ml of dry THF at 0° C. was added dropwise a solution of 32 g cis-exo-hexahydro-4,7-epoxyisobenzofuran-1,3-dione (mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. (1α,2β,3β,4α)-cis-exo-2-hydroxymethyl-3-chlorooxycarbonyloxymethyl-7-oxabicyclo[2.2.1]heptane and

C. (1α,2β,3β,4α)-cis-exo-7-oxabicyclo[2.2.1]heptane-2,3-dimethanol carbonate To a solution of 10 g title A diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title B compound as a crude oil.

This oil was dissolved in 30 ml of dry $CH_2Cl_2$ and cooled to −50° C. To this solution was added dropwise a solution of 10 ml pyridine in 10 ml $CH_2Cl_2$. It was stirred for 10 minutes and quenched with $H_2O$. The mixture was extracted thoroughly with $CH_2Cl_2$. The organic extract was dried over $MgSO_4$ and concentrated to give the title C cyclic carbonate as a crystalline solid (10.7 g).

D. (1α,2β,3β,4α)-cis-exo-2-hydroxymethyl-3-isopropyloxycarbonyloxymethyl-7-oxabicyclo[2.2.1]heptane A mixture of 10.7 g title C cyclic carbonate (58.1 mmole) in 100 ml isopropanol was refluxed for 24 hours. Excess isopropanol was removed under reduced pressure to give 14.4 g title D hydroxycarbonate as a viscous oil.

E. (1α,2β,3β,4α)-cis-exo-2-formyl-3-isopropyloxycarbonyloxymethyl-7-oxabicyclo[2.2.1]heptane To 5.0 g of title D alcohol D alcohol (20.5 mmol) in 65 ml of dry $CH_2Cl_2$ at 25° C. was added 13.2 Celite, 1.7 g NaOAc (6.15 mmole, 30 mole %) and 13.2 g pyridinium chlorochromate (61.5 mmole, 3 eq.). The mixture was stirred at 25° C. for 2 hours then diluted with 100 ml ether and filtered through a bed of fluorosil. The filtrate was concentrated to give 3.8 g of title E aldehyde as a clear oil which was used in the next reaction without further purification (78%).

F. [1α,2β(1R),3β,4α]-[3-[[(3-Isopropyloxycarbonyloxymethyl)-7-oxabicyclo[2.2.1]hept-2-yl]hydroxymethyl]phenyl]methoxymethyl ether and

G. [1α,2β(1S),3β,4α]-[3-[[(3-Isopropyloxycarbonyloxymethyl)-7-oxabicyclo[2.2.1]hept-2yl]hydroxymethyl]phenyl]methoxymethyl ether To 498.1 mg of magnesium turnings (20.5 mmole, 3 eq.) in 30 ml of dry THF at 45° C. was added 4.4 g 3-bromophenylmethoxymethylether and a crystal of iodine. The mixture was stirred at 45° C.–50° C. for 4 hours.

To a solution of 3.8 g title E aldehyde (15.7 mmole) in 20 ml of dry THF at −78° C. was added the above Grignard solution through a canula. The mixture was stirred at −78° C. under argon for 1.5 hours, quenched with saturated $NH_4Cl$ solution and the layers were separated. The aqueous layer was extracted with three 50 ml portions of $CH_2Cl_2$. The combined organic layer was dried over anhydrous $MgSO_4$ and concentrated to give a crude mixture which was separated on a silica gel column, eluting with 50% ether in hexanes to give 1.9 g of title F isomer and 800 mg of title G isomer.

H.

[1α,2β(1R),3β,4α]-[3-[[(3-Isopropyloxycarbonyloxymethyl)-7-oxabicyclo[2.2.1]hept-2-yl]acetoxymethyl]phenyl]methoxymethyl ether To 1.9 of title F alcohol (5 mmole) in 50 ml of pyridine was added 2.5 g acetic anhydride (25 mmole, 5 eq.) and a catalytic amount of 4-dimethylaminopyridine. The mixture was stirred at 25° C. for 1 hour and then concentrated. The residue was purified on a silica gel column eluting with 40% ether in hexanes to give 1.4 g title H acetate as a white solid (66.3%).

I.

(1α,2β,3β,4α)-[3-[[(3-Isopropyloxycarbonyloxymethyl)-7-oxabicyclo[2.2.1]hept-2-yl]methyl]phenyl]methoxymethyl ether A mixture of 1.2 g title H benzylacetate and 1.2 g of 10% palladium over carbon in 30 ml of acetic acid was shaken in a Parr bottle under 40 psi hydrogen pressure at 25° C. for 24 hours. TLC showed about 30% completion. The product and unreacted starting material were separated on a silica gel column, eluting with 30% ether in hexane. The unreacted starting material was again subjected to hydrogenolysis under the same conditions. Total yield: 520 mg of title I compound.

J.

(1α,2β,3β,4α)-[3-[[(3-Isopropyloxycarbonyloxymethyl)-7-oxabicyclo[2.2.1]hept-2-yl]methyl]phenol A mixture of 420 mg title I compound (1.43 mmole), 10 ml of 1N HCl and 10 ml THF was stirred at 25° C. for 48 hours. The mixture was neutralized by solid NaHCO$_3$ and extracted with three 50 ml portions of CH$_2$Cl$_2$, dried over MgSO$_4$ and concentrated to give 480 mg of title J compound in the form of a crude oil which was used directly in the next step.

K.

(1α,2β,3β,4α)-[3-[[(3-Isopropyloxycarbonyloxymethyl)-7-oxabicyclo[2.2.1]hept-2-yl]methyl]phenoxy]acetic acid, ethyl ester To a slurry of 39.7 mg of prewashed sodium hydride (1.6 mmole, 1.1 eq.) in 3 ml dimethoxy ether (DME) at 0° C. was added a solution of 480 mg title J compound (1.5 mmole) in 2 ml DME. The mixture was stirred at 0° C. for 15 minutes. To this mixture at 0° C. was added 375 mg of ethylbromoacetate (2.25 mmole, 1.5 eq.). The reaction mixture was warmed to 25° C. and stirred for an additional 20 minutes, then diluted with 30 ml ether, and filtered. The filtrate was concentrated and purified on a silica gel column eluting with 40% ether in hexanes to give 420 mg of title K compound as an oil.

L.

(1α,2β,3β,4α)-[3-[[3-Hydroxymethyl-7-oxabicyclo[2.2.1]-hept-2-yl]methyl]phenoxy]acetic acid and

M.

(1α,2β,3β,4α)-[3-[[3-Hydroxymethyl-7-oxabicyclo[2.2.1]-hept-2-yl]methyl]phenoxy]acetic acid, methyl ester To 420 mg of title K compound (1.03 mmole) in 2 ml H$_2$O and 8 ml THF at 0° C. was added 10 ml of 1N LiOH solution. The mixture was stirred while being warmed to 25° C. over a 3 hour period. THF was evaporated. The aqueous layer containing title L compound was extracted with three 10 ml portions of ether, then acidified to pH 3 with saturated oxalic acid, saturated with solid NaCl and extracted with three 20 ml portions of CH$_2$Cl$_2$. The extract was dried over MgSO$_4$ and concentrated to give a foam which was treated directly with excess CH$_2$N$_2$ in ether to give 260 mg of title M alcohol ester as an oil.

N.

(1α,2β,3β,4α)-[3-Formyl-7-oxabicyclo[2.2.1]-hept-2-yl]methyl]phenoxy]acetic acid, methyl ester To 1.3 ml pyridine (8.5 mmole, 10 eq.) in 30 ml CH$_2$Cl$_2$ at 25° C. was added 850 mg chromium trioxide (8.5 mmole. 10 eq.). The mixture was stirred for 30 minutes at 25° C. To this mixture was added a solution of 260 mg title M compound (0.85 mmole) in 5 ml CH$_2$Cl$_2$. The reaction mixture was stirred for 30 minutes then diluted with 100 ml ether, filtered through a bed of fluorosil and the filtrate concentrated to give 170 mg of title N aldehyde as an oil.

O.

(1α,2β,3β,4α)-[3-[[3-(3-Oxo-4,4-dimethyl-1-octenyl)-7-oxabicyclo[2.2.1]hept-2-yl]methyl]phenoxy]acetic acid, methyl ester To a slurry of 29.1 mg of 50% sodium hydride in mineral oil (0.61 mmole, 1.1 eq.) in 15 ml DME at 0° C. under argon was added 215 mg of 2-oxo-3,3-dimethylheptyl dimethylphosphonate (0.84 mmole, 1.5 eq.). The mixture was stirred at 25° C. for 1 hour, then cooled to 0° C. and to it was added a solution of 170 mg title N aldehyde (0.56 mmole) in 5 ml DME. The reaction mixture was stirred for 2 hours, quenched with glacial acetic acid and concentrated. The residue was taken up in 50 ml ether and washed with two 20 ml portions of saturated NaHCO$_3$, 20 ml H$_2$O, dried over MgSO$_4$ and concentrated to give a crude oil which was purified on a silica gel column, eluting with 40% ether in hexanes to give 180 mg title O enone as an oil.

P.

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]acetic acid, methyl ester and

Q.

[1α,2β,3β(1E,3S),4α]-[3-[[3-(3-Hydroxy-4,4-dimethyl-1-octenyl)-7-oxabicyclo[2.2.1]hept-2-yl]methyl]phenoxy]acetic acid, methyl ester To 180 mg title O enone (0.42 mmole) in 2 ml MeOH and 5 drops THF was added 155 mg CeCl$_3$ (0.42 mmole, 1 eq.). The mixture was stirred at 25° C. for 10 minutes, cooled to 0° C. and to it was added 15.8 mg NaBH$_4$ (0.42 mmole, 4 eq.). The reaction mixture was stirred at 0° C. for 10 minutes, then poured into 100 ml of saturated NH$_4$Cl, extracted with three 30 ml portions of ether, dried over MgSO$_4$ and concentrated to give a crude oil which was separated on a silica gel column, eluting with 50% ether in hexanes to give 120 mg of title P compound and 30 mg of title Q compound.

EXAMPLE 2

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]acetic acid.

To 120 mg Example 1, title P ester (0.28 mmole) in 16 ml THF and 4 ml H$_2$O at 0° C. was added dropwise 2.8 ml of 1M LiOH. The mixture was warmed to 25° C. and stirred for 1 hour. THF was evaporated and the residue was diluted with 10 ml H₂O, acidified to pH 3 with oxalic acid and extracted with three 20 ml portions of ether. The ethereal extracts were washed with two 10 ml portions of H₂O and 20 ml brine, dried over MgSO₄ and concentrated to give the title compound as an oil.

This oil was put under high vacuum for 1 day to give 101 mg of the title acid.

Anal. Calcd for $C_{25}H_{36}O_5$, 0.2 mole $H_2O$:C, 71.46; H, 8.73; Found: C, 71.41; H, 8.78.

TLC: silica gel; 10% MeOH/CH₂Cl₂; $R_f \sim 0.44$.

EXAMPLE 3

(1β,2β,3α,4β)-[3-[[3-(3-Hydroxy-4,4-dimethyloctyl)-7-oxabicyclo[2.2.1]hept-2-yl]methyl]phenoxy]acetic acid, methyl ester

A.

(1β,2β,3α,4β)-[3-[[3-(3-Oxo-4,4-dimethyloctyl)-7-oxabicyclo[2.2.1]hept-2-yl]methyl]phenoxy]acetic acid, methyl ester To a solution of 428 mg (1 mmole) of [1β,2β,3α(-1E),4β]-[3-[[3-(3-oxo-4,4-dimethyl-1-octenyl)-7-oxabicyclo[2.2.1]hept-2-yl]methyl]phenoxy]acetic acid, methyl ester in 15 ml of pyridine is added with stirring 38 mg of sodium borohydride (1 mmole). After 3 days at room temperature, the reaction mixture is poured into 50 ml of water containing 10 ml of a 10% potassium acetate solution. The reaction mixture is extracted with ether. The ether extract is washed with 1N aqueous hydrochloric acid solution, water, dried over anhydrous magnesium sulfate and finally is concentrated in vacuo to give the title A ketone.

B.

(1β,2β,3α,4β)-[3-[[3-(3-Hydroxy-4,4-dimethyloctyl)-7-oxabicyclo[2.2.1]hept-2-yl]methyl]phenoxy]acetic acid Following the procedure of Example 1, Parts P and Q, except substituting for the Example 1 title O enone, the Example 3 title A ketone, the title compound is obtained.

EXAMPLE 4

(1β,2β,3α,4β)-[3-[[3-(3-Hydroxy-4,4-dimethyloctyl)-7-oxabicyclo[2.2.1]hept-2-yl]methyl]phenoxy]acetic acid.

Following the procedure of Example 2 except substituting the Example 3 ester for the Example 1 ester, the title acid is obtained.

EXAMPLE 5

[1α,2β,3β(1E,3R),4α]-[3-[[3-(3-Hydroxy-4,4,-dimethyl-1-octenyl)-7-oxabicyclo[2.2.1]hept-2-yl]methyl]phenoxy]propionic acid, methyl ester Following the procedure of Example 1, except substituting ethylbromopropionate for ethylbromoacetate, the title compound is obtained.

EXAMPLE 6

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]propionic acid Following the procedure of Example 2, except substituting the Example 5 ester for the Example 1 ester, the title acid is obtained.

Example 7

[1α,2β,3β(1E,3R),4α]-[3-[[3-(3-Hydroxy-4,4-dimethyl-1-octenyl)-7-oxabicyclo[2.2.1]hept-2-yl]ethyl]phenoxy]acetic acid

A.

(1α,2β,3β,4β)-[Cis-exo-3-isopropyloxycarbonyloxymethyl-7-oxabicyclo[2.2.1]hept-2-yl]acetaldehyde Into a dry 1000 ml round bottom 3-necked flask containing a stir bar is added dried 12.9 g (37.7 mmoles) methoxymethyltriphenylphosphonium chloride $((C_6H_5)_3P^+—CH_2OCH_3Cl^-)$ and 235 ml distilled toluene (stored over molecular sieves). The resulting suspension is stirred in an ice-bath, under argon, until cold and then a 1.55M solution of 18.3 ml (28.3 mmol) of potassium t-amylate in toluene is added dropwise. A bright red solution forms which is stirred at 0° C. for an additional 35 minutes. Therefore, a solution of 4.81 g (18.8 mmol) of Example 1 title E aldehyde in 60 ml toluene is added by means of a dropping funnel over a 35 minute period with the ice-bath still in place. The reaction is then quenched by addition of 2.3 g (39 mmol) acetic acid in 5 ml ether. The reaction mixture immediately turns pale yellow and is immediately poured into 200 ml saturated NH₄Cl, and extracted with ether (4×200 ml). The combined ether phases are washed with NaCl, saturated solution, and dried (MgSO₄) and concentrated to yield an oil in a white crystalline solid (phosphine oxide). The reaction mixture is triturated with ether and the precipitated phosphine oxide is filtered off. Ether solution is concentrated under reduced pressure, dissolved in THF and treated with 10% aqueous hydrochloric acid solution. After stirring for one hour at room temperature, solid sodium bicarbonate is added to the reaction mixture. The THF solution is dried over anhydrous magnesium sulfate and concentrated under reduced pressure. The crude residue is purified on a LPS-1 silica gel column with ethyl acetate in hexane to obtain the title A aldehyde.

B.

[(1α,2β,3β(1E,3R),4α]-[3-[[3-(3-Hydroxy-4,4-dimethyl-1-octenyl)-7-oxabicyclo[2.2.1]hept-2-yl]ethyl]phenoxy]acetic acid Following the procedure of Examples 1, Parts F–Q, and 2 except substituting the above part A aldehyde for the aldehyde of Example 1, Part E, the title compound is obtained.

EXAMPLE 8

[1α,2β,3β(1E,3R),4α]-[3-[[3-(3-Hydroxy-4,4-dimethyl-1-octenyl)-7-oxabicyclo[2.2.1]hept-2-yl]propyl]phenoxy]acetic acid

A.

(1α,2β,3β,4α]-[Cis-exo-3-isopropyloxycarbonyloxymethyl-7-oxabicyclo[2.2.1]hept-2-yl]propionaldehyde Following the procedure of Example 7, Part A except substituting the Example 7, title A compound for Example 1 title E aldehyde, the title aldehyde is obtained.

B.

[1α,2β,3β(1E,3R),4α]-[3-[[3-(3-Hydroxy-4,4-dimethyl-1-octenyl)-7-oxabicyclo[2.2.1]hept-2-yl]propyl]phenoxy]acetic acid Following the procedure of Examples 1 and 2 except substituting the title A aldehyde for the aldehyde of Example 1, Part E, the title compound is obtained.

EXAMPLE 9

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]butanoic acid Following the procedure of Examples 1 and 2 except substituting ethylbromobutanoate for ethylbromoacetate, the title compound is obtained.

EXAMPLE 10

[1α,2β,3β(1E,3R),4α]-[3-[[3-Hydroxy-4,4-dimethyl-1-octenyl)-7-oxabicyclo[2.2.1]hept-2yl]methyl]phenoxy]pentanoic acid Following the procedure of Examples 1 and 2 except substituting ethylbromopentanoate for ethylbromoacetate, the title compound is obtained.

EXAMPLE 11

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]propionoic acid Following the procedure of Examples 1 and 2 except substituting ethylbromopropionoate for ethylbromoacetate, the title compound is obtained.

EXAMPLE 12

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]hexanoic acid Following the procedure of Examples 1 and 2 except substituting ethylbromohexanoate for ethylbromoacetate, the title compound is obtained.

EXAMPLE 13

[1α,2β,3β(1E,3R),4α]-[3-[[3-(3-Hydroxy-4,4-dimethyl-1-octenyl)-7-oxabicyclo[2.2.1]hept-2-yl]methyl]phenoxy]octanoic acid Following the procedure of Examples 1 and 2 except substituting ethylbromooctanoate for ethylbromoacetate, the title compound is obtained.

EXAMPLE 14

(1β,2β,3α,4β)-[3-[[3-(3-Hydroxy-4,4-dimethyloctyl)-7-oxabicyclo[2.2.1]hept-2-yl]methyl]phenoxy]butanoic acid Following the procedure of Examples 1, 3 and 4 except substituting ethylbromobutanoate for ethylbromoacetate, the title compound is obtained.

EXAMPLE 15

(1β,2β,3α,4β)-[3-[[3-(3-Hydroxy-3-phenylpropyl)-7-oxabicyclo[2.2.1]hept-2-yl]methyl]phenoxy]acetic acid Following the procedure of Examples 1, 3 and 4 except substituting 2-oxo-phenethyl dimethylphosphonate for 2-oxo-3,3-dimethylheptyl dimethyl phosphonate, the title compound is obtained.

EXAMPLE 16

(1β,2β,3α,4β)-[3-[[3-(3-Hydroxy-cyclohexylpropyl)-7-oxabicyclo[2.2.1]hept-2-yl]methyl]phenoxy]acetic acid Following the procedure of Examples 1, 3 and 4 except substituting 2-oxo-cyclohexylethyl dimethyl phosphonate for 2-oxo-3,3-dimethylheptyl dimethyl phosphonate, the title compound is obtained.

EXAMPLE 17

(1β,2β,3α,4β)-[3-[[3-(3-Hydroxy-4,4-dimethyloctyl)-7-oxabicyclo[2.2.1]hept-2-yl]methyl]phenoxy]pentanoic acid Following the procedure of Examples 1, 3 and 4 except substituting ethylbromopentanoate for ethylbromoacetate, the title compound is obtained.

EXAMPLE 18

(1β,2β,3α,4β)-[3-[[3-(3-Hydroxy-4,4-dimethyloctyl)-7-oxabicyclo[2.2.1]hept-2-yl]methyl]phenoxy]propionoic acid Following the procedure of Examples 1, 3 and 4 except substituting ethylbromopropionate for ethylbromoacetate, the title compound is obtained.

EXAMPLE 19

[1α,2β,3β(1E,3R),4α]-[4-[[3-(3-Hydroxy-4,4-dimethyl-1-oxtenyl)-7-oxabicyclo[2.2.1]hept-2-yl]methyl]phenoxy]acetic acid Following the procedure of Examples 1 and 2 except substituting 4-bromophenylmethoxymethyl ether for 3-bromophenylmethoxymethyl ether, the title acid is obtained.

EXAMPLE 20

[1α,2β,3β(1E,3R),4α]-[2-[[3-(3-Hydroxy-4,4-dimethyl-1-octenyl)-7-oxybicyclo[2.2.1]hept-2-yl]methyl]phenoxy]acetic acid Following the procedure of Examples 1 and 2 except substituting 2-bromophenylmethoxymethyl ether for 3-bromophenylmethoxymethyl ether, the title acid is obtained.

EXAMPLE 21

[1α,2β,3β(1E,3R), 4α]-[4-[[3-(3-Hydroxy-4,4-dimethyl-1-octenyl)-7-oxabicyclo[2.2.1]hept-2-yl]methyl]phenoxy]propionic acid Following the procedure of Examples 1 and 2 except substituting ethylbromopropionate for ethylbromoacetate and substituting 4-bromophenylmethoxymethyl ether for 3-bromophenylmethoxymethyl ether, the title acid is obtained.

EXAMPLE 22

[1α,2β,3β(1E,3R),4α]-[2-[[2-(3-Hydroxy-phenylpropyl)-7-oxabicyclo[2.2.1]hept-2-yl]methyl]phenoxy]acetic acid Following the procedure of Examples 1 and 2 except substituting 2-bromophenylmethoxymethyl ether for 3-bromophenylmethoxymethyl ether and substituting 2-oxophenethyldimethylphosphonate for 2-oxo-3,3-dimethyl heptyl dimethylphosphonate, the title acid is obtained.

EXAMPLE 23

1α,2β,3β(1E,3R),4α]-[3-[[3-(3-Hydroxy-4,4-dimethyl-1-octenyl)-7-oxabicyclo[2.2.1]hept-2-yl]ethyl]phenoxy]butanoic acid Following the procedure of Examples 7, 1 and 2 except substituting ethylbromobutanoate for ethylbromoacetate, the title acid is obtained.

EXAMPLE 24

[1α,2β,3β(1E,3R),4α]-[3-[[3-(3-Hydroxy-4,4-dimethyl-1-octenyl)-7-oxabicyclo[2.2.1]hept-2-yl]ethyl]phenoxy]pentanoic acid Following the procedure of Examples 7, 1 and 2 except substituting ethylbromopentanoate for ethylbromoacetate, the title acid is obtained.

EXAMPLE 25

[1α,2β,3β(1E,3R),4α]-[3-[[3-(3-Hydroxy-3-phenylpropyl)-7-oxabicyclo[2.2.1]hept-2-yl]ethyl]phenoxy]acetic acid Following the procedure of Examples 7, 1 and 2 except substituting 2-oxo-phenethyl dimethylphosphonate for 2oxo-3,3-dimethylheptyldimethylphosphonate, the title acid is obtained.

EXAMPLE 26

[1α,2β,3β(1E,3R),4α]-[3-[[3-(3-Hydroxycyclohexylpropyl)-7-oxabicyclo[2.2.1]hept-2-yl]ethyl]phenoxy]butanoic acid Following the procedure of Examples 7, 1 and 2 except substituting ethylbromopentanoate for ethylbromoacetate and substituting 2-oxo-cyclohexylethyl dimethylphosphonate for 2-oxo-3,3-dimethylheptyl dimethylphosphonate, the title acid is obtained.

EXAMPLE 27

(1β,2β,3α4β)-[3-[[3-(3-Hydroxy-4,4-dimethyloctyl)-7-oxabicyclo[2.2.1]hept-2-yl]ethyl]phenoxy]pentanoic acid Following the procedure of Examples 7, 1, 3 and 4, except substituting ethylbromopentanoate for ethylbromoacetate, the title acid is obtained.

EXAMPLE 28

[1α,2β,3β(1E,3R),4α]-[3-[[3-(3-Hydroxy-4,4-dimethyl-1-octenyl)-7-oxabicyclo[2.2.1]hept-2-yl]butyl]phenoxy]acetic acid

A.

(1α,2β,3β,4α)-[Cis-exo-3-isopropyloxycarbonyloxymethyl-7-oxabicyclo[2.2.1]hept-2-yl]butyraldehyde Following the procedure of Example 7, part A, except substituting Example 8, part A aldehyde (prepared in Example 7, part A) for the Example 1, part E aldehyde, the title aldehyde is obtained.

B.

[1α,2β,3β(1E,3R),4α]-[3-[[3-(3-Hydroxy-4,4-dimethyl-1-octenyl)-7-oxabicyclo[2.2.1]hept-2-yl]butyl]phenoxy]acetic acid Following the procedure of Example 7, part B, except substituting the aldehyde from part A above, for Example 8, part A aldehyde, the title aldehyde is obtained.

EXAMPLE 29

[1α,2β,3β(1E,3R),4α]-[3-[[3-(3-Hydroxy-4,4-dimethyl-1-octenyl)-7-oxabicyclo[2.2.1]hept-2-yl]butyl]phenoxy]butanoic acid Following the procedure of Examples 28, 1 and 2, except substituting ethylbromobutanoate for ethylbromoacetate, the title acid is obtained.

EXAMPLE 30

[1α,2β,3β(1E,3R),4α]-[3-[[3-(3-Hydroxy-3-phenylbutyl)-7-oxabicyclo[2.2.1]hept-2-yl]propyl]phenoxy]butanoic acid Following the procedure of Examples 28, 1 and 2, except substituting 2-oxo-phenethyl dimethylphosphonate for 2-oxo-3,3-dimethylheptyl dimethylphosphonate, the title acid is obtained.

EXAMPLE 31

[1α,2β,3β(1E,3R),4α]-[3-[[3-(3-Hydroxy-cyclohexyl butyl)-7-oxabicyclo[2.2.1]hept-2-yl]propyl]phenoxy]pentanoic acid Following the procedure of Examples 28, 1 and 2, except substituting ethylbromopentanoate for ethylbromoacetate and substituting 2-oxo-cyclohexylethyl dimethylphosphonate for 2-oxo-3,3-dimethylheptyl dimethylphosphonate, the title acid is obtained.

What is claimed is:

1. A compound having the structural formula

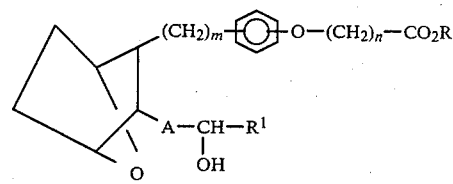

and including all stereoisomers thereof;
wherein

A is CH=CH or $(CH_2)_2$;

m is 1 to 4; n is 1 to 8; R is H, lower alkyl or alkali metal; and $R^1$ is lower alkyl, aryl, aralkyl, cycloalkyl or cycloalkylalkyl; wherein the term lower alkyl or alkyl by itself or as part of another group is unsubstituted or substituted with halo, trifluoromethyl, alkoxy, aryl, alkyl-aryl, haloaryl, cycloalkyl or alkylcycloalkyl;

the term aryl by itself or as part of another group contains 6 to 10 carbons and is unsubstituted or substituted with lower alkyl, halogen or lower alkoxy; and the term cycloalkyl by itself or as part of another group contains 3 to 12 carbons and is unsubstituted or substituted with 1 or 2 halogens, 1 or 2 lower alkyl groups and/or 1 or 2 lower alkoxy groups; and wherein $(CH_2)_m$ and $(CH_2)_n$ may be substituted by one or more alkyl substituents.

2. The compound as defined in claim 1 having the formula

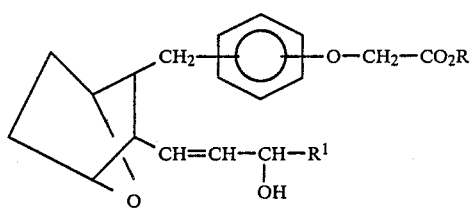

wherein R is hydrogen, R¹ is lower alkyl, including all stereoisomers thereof.

3. The compound as defined in claim 1 having the formula

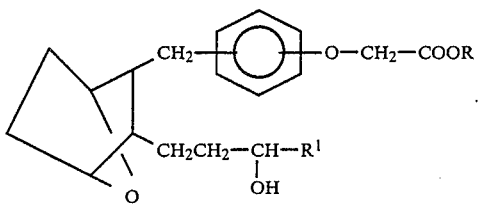

4. The compound as defined in claim 1 wherein m is 1 and n is 1.

5. The compound as defined in claim 1 wherein A is CH=CH.

6. The compound as defined in claim 4 wherein R¹ is butyl, pentyl, hexyl, heptyl or 1,1-dimethylpentyl.

7. The compound as defined in claim 1 having the name [1α,2β,3β(1E,3R),4α]-[3-[[3-(3-hydroxy-4,4-dimethyl-1-octenyl)-7-oxabicyclo[2.2.1]hept-2-yl]methyl]phenoxy]acetic acid or the methyl ester thereof, including all stereoisomers thereof.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier thereof.

11. A method of inhibiting bronchoconstriction associated with asthma, which comprises administering to a mammalian host an effective amount of a compound as defined in claim 1 or a pharmaceutically acceptable salt thereof.

12. A method for treating peripheral vascular disease, which comprises topically or systemically administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,522,949

DATED : 6/11/85

INVENTOR(S) : Jagabandhu Das et al.

It is certified that error appears in the above—identified patent and that said Letters Patent is hereby corrected as shown below:

```
Column 9, line 46, after "[3-[[3-" insert --(3- --.
Column 12, line 8, after "[3-" insert --[[3- --.
Column 14, line 8, "4β" should read --4α--.
Column 14, line 21, "Therefore" should read --thereafter--.
```

Signed and Sealed this

Twenty-second Day of October 1985

[SEAL]

Attest:

DONALD J. QUIGG

Attesting Officer

*Commissioner of Patents and Trademarks—Designate*